United States Patent [19]

Yoo

[11] 3,940,447

[45] Feb. 24, 1976

[54] PROCESS FOR HYDROFORMYLATION OF OLEFIN HYDROCARBONS

[75] Inventor: Jin Sun Yoo, South Holland, Ill.

[73] Assignee: Atlantic Richfield Company, Los Angeles, Calif.

[22] Filed: Dec. 7, 1973

[21] Appl. No.: 422,957

Related U.S. Application Data

[63] Continuation of Ser. No. 32,411, April 27, 1970, abandoned.

[52] U.S. Cl. ...... 260/604 HF; 260/632 HF; 260/602
[51] Int. Cl.² .......................................... C07C 45/08
[58] Field of Search .............................. 260/604 HF

[56] References Cited
UNITED STATES PATENTS

3,352,924  11/1967  Gladrow et al. ............... 260/604 HF

FOREIGN PATENTS OR APPLICATIONS

1,332,893  10/1973  United Kingdom .......... 260/604 HF

OTHER PUBLICATIONS

Robinson et al., Journ. of Catalysis, Vol. 15, 1969, pp. 245–249.

Brown et al., Journ. of the Chemical Soc. A, 1970, pp. 2753–2764.

*Primary Examiner*—James O. Thomas, Jr.
*Assistant Examiner*—R. H. Liles
*Attorney, Agent, or Firm*—John R. Ewbank

[57] ABSTRACT

A new, solid catalyst suitable for the hydroformylation of low molecular weight olefins is disclosed. The catalyst composition is a hydrido-platinum group metal carbonyl-Group VA electron donor ligand complex on a solid, sodium form natural or synthetic crystalline aluminosilicate support.

9 Claims, No Drawings

PROCESS FOR HYDROFORMYLATION OF OLEFIN HYDROCARBONS

This is a continuation application of application Ser. No. 32,411, filed Apr. 27, 1970, now abandoned.

This invention relates to a new solid catalyst composition suitable for the hydroformylation, including hydroxyhydroformylation, of low molecular weight olefins to form the corresponding aldehydes and alcohols.

Processes directed to the production of reaction mixtures comprising substantial amounts of aldehydes and at times lesser amounts of alcohols by the reaction of olefinic compounds with carbon monoxide and hydrogen at elevated temperatures and pressures in the presence of certain catalysts are well known in the art. The aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with the consequent variation in the products obtained. These processes known in the industry, and referred to herein as hydroformylation, involve reactions which may be shown in the general case by the following equation:

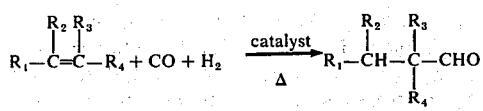

and/or

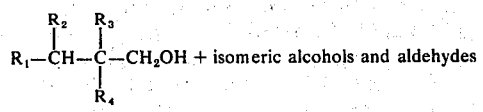

In the above equation, each R represents an organic radical, for example hydrocarbyl, or a suitable atom such as hydrogen or a halogen. The above reaction is similarly applied to an olefinic linkage in a cycloaliphatic ring.

U.S. Pat. No. 3,239,566, issued Mar. 8, 1966, discloses a homogeneous rhodium catalyst suitable for use in the hydroformylation of olefins. The catalyst consists of a complex of rhodium with carbon monoxide and a trialkyl phosphine ligand. While the catalyst of that patent offers advantages over other prior art catalytic systems, the homogeneous system disclosed therein still does not offer the activity, stability and long-life requirements of commercial processing.

U.S. Pat. No. 3,487,112 to Paulik et al., issued December 30, 1969, discloses a heterogeneous catalyst system for the hydroformylation of olefins. The catalyst system disclosed therein is a rhodium-halogen-carbonyl-trialkyl phosphine complex supported on an inert base. The inert support can be a number of materials such as alumina, silica, carbon or a zeolite.

It is an object of this invention, therefore, to provide a novel catalyst system for the hydroformylation, including hydroxyhydroformylation, of olefins. More specifically, it is an object of this invention to provide a novel, heterogeneous, solid phase catalytic system for the hydroformylation of low molecular weight olefins to form the corresponding alcohols and aldehydes under relatively mild reaction conditions.

A solid phase catalyst is highly desirable for a number of reasons, including the ease of handling of solids as contrasted with liquids. In addition, a solid catalyst could be more readily and completely separated from the low molecular weight alcohols and aldehydes commonly produced by such catalysts. When surface phenomena are considered, a solid phase catalyst might also be more active and more selective than the homogeneous solution type of the same general ingredients.

It has been found that a solid catalyst of a hydrido-platinum-group metal (e.g., platinum, palladium, rhodium and ruthenium) carbonyl with an electron donor ligand or organic-substituted elements of Group VA of the periodic table, said elements having an atomic weight of 7 to 83, on a solid, sodium form natural or synthetic crystalline aluminosilicate support, provide a solid phase composition having highly desirable physical and chemical characteristics and when hydrocarbonylated posses excellent catalytic activity and selectivity for the hydroformylation, including hydroxyhydroformylation, of low molecular weight olefins. To obtain such solids the catalyst-forming reactants can be combined in a molar ratio of electron donor ligand to platinum-group metal of about 1 to 4:1, preferably about 1.5 to 3:1, although either the platinum-group metal or the ligand, preferably the ligand, can be present in excess. The platinum-group metal and electron donor ligand are present on the support in a minor, catalytically effective amount and the catalyst can contain the platinum-group metal in amounts of, for example, from about 0.05 to 1 weight percent, preferably 0.05 to 0.5 weight percent of the catalyst.

In the preparation of the catalyst composition of the present invention, the platinum-group metal source is provided by compounds of the metal which are at least slightly soluble in some solvent wherein the metal-group VA ligand complex can be formed. Preferred are the weak field complexes, the ligands of which readily serve in solution as transfer agents. Suitable sources of the metal can include, for example, halides, e.g., $MCl_n$, $MBr_n$, $MI_n$, where M represents the platinum-group metal and n (here and below) is the available valence of the platinum-group metal; dihydrocarbyl derivatives, i.e., $M(OR)_n$, where R represents alkyl, aryl, aralkyl, and the like groups; dihydrocarbyloxy metal carboxylates, i.e., $(RO)_nMOOCR'$ where R and R' are as defined above as R; diphosphine complexes, e.g. $(M[(C_6H_5)_2PC_2H_4P(C_6H_5)_2]X_2$, where X is a halide. Also available as metal sources are chelates formed by the metal and weak field ligands, such as $\beta$-diketones or $\beta$-keto-carboxylic acid esters and salts of carboxylic acids. Examples of these types of metal sources include $\beta$-diketonato-M (II), acetylacetonato-M (II), propylacetonato-M (II), benzoylacetonato-M; chelates from $\beta$-ketocarboxylic acid esters; salts of saturated monocarboxylic acids, e.g. the platinum-group metal formate, propionate, caproate, octoate, palmitate, stearate, phenylacetate, phenylpropionate, and the like; salts of corresponding unsaturated monocarboxylic acids, e.g. the platinum-group metal acrylate, vinyl acetate, and the like; salts of saturated dicarboxylic acids, e.g. the platinum-group metal adipate, decane-1, 10-dicarboxylate, and the like; salts of corresponding unsaturated dicarboxylic acids, e.g., the platinum-group metal muconate and the like; salts of cycloaliphatic and aromatic carboxylic acids, e.g., the platinum-group metal cyclohexane carboxylate, benzoate, phthalates, and the like; and alkoxycarboxylates, e.g., the platinum-group metal dimethoxyacetate and the like. Preferred as the platinum-group metal is rhodium and preferred as the source of rhodium is rhodium acetylacetonate.

The electron donor ligand component employed in preparing the metal complex component of the catalyst of the present invention is preferably a triorganophosphine corresponding to the general formula $R_3P$ wherein R is a hydrocarbon radical, e.g. alkyl, aryl, alkaryl, aralkyl and cycloalkyl, of from 1 to about 20 carbon atoms, preferably 2 to about 6 carbon atoms and devoid of olefinic or acetylenic unsaturation; different R groups may, of course, be present in the same phosphine molecule. When the phosphine component contains aromatic groups it is generally preferred that these have mono-cyclic structures, e.g., that the groups be selected from phenyl, alkylphenyl or phenylalkyl radicals.

Multifunctional phosphines of the formula $R_2P-(CH_2)_n-PR_2$ such as bis(diphenylphosphine)ehtane, may be used in place of the foregoing described unidentate phosphines. Phosphines may also be replaced by other electron donor ligands such as, for example, alkyl, aryl, alkaryl, aralkyl, or cycloalkyl phosphites, arsines, stibines or bismuthines. Other monodentate or bidentate ligands containing nitrogen donating centers such as pyridine or alpha, alpha-bipyridyl, may also be utilized. It is, however, preferred that triorganophosphines be utilized. Examples of suitable phosphines for the composition of the present invention are triphenylphosphine, trimethylphosphine, tricyclohexylphosphine, tri-n-hexylphosphine, tri-n-decylphosphine, tribenzylphosphine, tri-(4-n-butylphenyl) phosphine, and the like. Generally speaking, the electron donor ligand compounds of Group VA elements of the periodic table, having atomic numbers of 7 to 83 can be used in the catalysts.

The solid support of the catalyst of the present invention can be a natural or synthetic sodium form crystalline aluminosilicate having pore diameters of from about 6 to 15 Angstroms, preferably from about 10 to 14 Angstroms, a silica-to-alumina mole ratio of from about 2:1 to 12:1, preferably from about 4:1 to 6:1 and a sodium oxide to aluminum oxide mole ratio of from about 0.7:1 to 1.1:1, preferably from about 0.9:1 to 1:1. The aluminosilicate is preferably in the uncalcined, deliquescent form. The sodium aluminosilicate can have a minor portion of the sodium exchanged with another metal, e.g. a polyvalent metal, or hydrogen but the sodium aluminosilicate present in the catalyst generally has at least about 5 weight percent sodium, preferably at least about 8 weight percent, on a non-hydrated basis.

The crystalline aluminosilicate-based support can also contain minor amounts of other suitable materials such as hydrous alumina, silica-alumina hydrogel, silica-alumina xerogel and oxides of suitable metals such as the metals of Groups II, III and IV of the Periodic Table. The crystalline aluminosilicate-based support can be fabricated into macrosize form, if desired, of a size of about 1/64 to ½ inch or more in diameter and about 1/32 to 1 inch or more in length.

The preparation of the overall catalyst composition is preferably conducted by first forming the complex of the electron donor ligand and the platinum-group metal source, e.g., rhodium acetylacetonate, rhodium chloride, palladium acetylacetonate and the like. The platinum-group metal source and ligand can be present in about the stoichiometric amounts necessary to form the complex or one component can be present in an excess amount of that necessary for the formation of the complex.

Formation of the ligand-platinum-group metal complex may be effected by simply mixing the two reactants in the presence of a suitable solvent for the complexing reaction. The mixing may be done at room temperature or up to as high as about 300°F. The complex usually forms within about 20 to 40 minutes after mixing at elevated temperature. Suitable solvents for the complex-forming reaction include the same solvents which are suitable for use in the final catalyst composition. If desired, however, the complexing may be accomplished in a solvent which is unsuitable for use in the final composition; in this case the resultant complex will first be isolated from the reaction mixture and redissolved, or re-suspended, in a proper solvent which is inert to the final catalyst composition.

Thus, for example, one method of preparing a phosphine-rhodium complex can involve stirring, preferably at room temperature, a mixture of tri-n-butylphosphine, rhodium chloride and chlorobenzene. In another method, the complex may be prepared by refluxing an alcohol, e.g. ethanol, solution of the phosphine, say tri-n-butylphosphine, and rhodium acetylacetonate, preferably at room temperature of about 150° to 250°F., and isolating the resultant complex from the reactant mixture. This approach is often preferred where the metal reagent contains some water of hydration, as the water will be removed from the complex when the latter is separated from the alcohol solvent.

In either case, the platinum-group metal triorganophosphine complex can be dissolved in a suitable solvent, e.g., ethanol, methanol, benzene, chlorobenzene, or the like, and charged to a reactor. Hydrogen and carbon monoxide gas can then be introduced separately, or as a premixed gas, in a molar ratio of hydrogen to carbon monoxide of from about 1:1 to 5:1, preferably from about 1.2:1 to 3.5:1, at a temperature of from about 60° to 400°C., preferably from about 150° to 250°C., and a pressure of from about 500 to 3000 psig., preferably from about 700 to 1,800 psig. to obtain the hydrido-platinum-group metal carbonyltriorgano phosphine complex. The solid support, in finely-divided form, is added to the complex in the solvent and the system is agitated for a time sufficient to affix the complex on the support. When the platinum-group metal source is a halide, such as rhodium chloride, the excess sodium present in the sodium form crystalline aluminosilicate support reacts or combines with the halide to form a compound, such as sodium chloride, which is not affixed to the support.

The solid supported catalyst can also be prepared in situ by charging the metal source, such as rhodium acetylacetonate, the electron donor ligand, such as tributyl phosphine or triphenyl phosphine, and the support in finely-divided form in a suitable solvent to an autoclave reactor and allowing these components to react under a premixed gas of hydrogen and carbon monoxide of a molar ratio of hydrogen to carbon monoxide of from about 1:1 to 5:1 at a pressure of from about 500 to 3,000, preferably 700 to 1800, psig., and a temperature of from about 150° to 195°C. for about one hour. The resulting supported catalyst system can be separated by removing the liquid phase from the reactor. If desired, the low molecular weight olefin can be charged to the catalyst system before separation and the hydroformylation reaction carried out in the presence of the solvent. After the reaction is completed, the liquid reaction mixture can be separated and removed from the reactor. Alternatively, the catalyst components, support and low molecular weight olefin can be charged simultaneously in a solvent to the autoclave under conditions as set forth above, thus allowing the system to simultaneously undergo formation of the solid supported catalyst system and the hydroformylation of the low molecular weight olefin.

The solid supported catalyst system can also be prepared by dissolving the metal source such as a platinum-group metal naphthenate, acetylacetonate or chloride in a solvent such as benzene or alcohol. The solid support is added to the resulting solution and the system is agitated at room temperature overnight yielding an supernatant liquid and support particles. These platinum-group metal-impregnated support particles are then filtered, washed and dried in an oven. The dried platinum-group metal-impregnated particles are charged to a reactor along with an electron donor ligand, such as tributyl phosphine, in a solvent. The system is pressured with hydrogen and carbon monoxide under conditions as set forth above for in situ preparation and the hydrido-platinum-group metal carbonyl-triorgano phosphine complex on a solid, sodium form crystalline aluminosilicate support catalyst recovered. An olefin feed can be introduced with the hydrogen and carbon monoxide also in the manner set forth above for in situ preparation.

The supported catalyst composition of the present invention is effective for hydroformylation, including hydroxyhydroformylation, of olefinic hydrocarbons, e.g., of 2 to about 16 carbon atoms, preferably 3 to 10 carbon atoms, and is highly desirable for such uses. For example, it is possible to provide alcohols, aldehydes, and the like from aliphatic mono-olefins. Of particular interest, however, is the selective activity of the present catalyst composition in the hydroformylation of pentene to form hexanol and hexanal. The selectivity of the catalyst of the present invention is exceptional for this type of reaction, while the activity is high as well, resulting in greater efficiency in producing such alcohols and aldehydes. In the prior art, such alcohols are produced in rather minor amounts. With the present catalyst, it is possible to obtain such alcohols, e.g., n-hexanol and isohexanol as the major product.

Hydroformylation, including hydroxyhydroformylation, can generally be effected by contacting the olefinically-unsaturated feed with hydrogen and carbon monoxide, for instance, under elevated pressure and in the presence of the catalyst at a temperature of about 100° to 350°C., preferably about 150° to 200° or 250°C. Elevated temperatures ordinarily can be maintained by the heat of reaction without external heating means. In many cases, it may be necessary to control the temperature by cooling, as for example, by circulating a cooling medium through heat exchange tubes in the reactor. Pressures of up to about 3,000 or more psig., preferably about 500 to 2,000 psig. or even about 700 to 1,800 psig., are suitable with the catalyst composition of the present invention. The amount of catalyst composition used in the reaction is that sufficient to effect hydroformylation or hydroxyhydroformylation of the feed and often the olefin feed contacts the catalyst at the rate of about 1 to about 20, preferably 1 to 10, WHSV (weight of olefin per weight of catalyst per hour). The process is applicable to continuous processing, e.g., with a catalyst slurry or a fixed bed, as well as batch processes. The hydrogen and carbon monoxide are preferably introduced into the reactor, for instance as a premixed gas, in a molar ratio of hydrogen to carbon monoxide from about 1.1:1 to 5:1, preferably from about 1.2:1 to 3.5:1. The catalyst system of the instant invention can be readily regenerated by the addition of a fresh triorgano phosphine ligand to the deactivated catalyst.

EXAMPLE I

Chlorotris(triphenylphosphine)rhodium(I) (0.5 m mole) [$(\phi_3P)_3RhCl$], was dissolved in 50 ml benzene in a 300 cc autoclave, and 20 g of uncalcined deliquescent sodium type Y crystalline aluminosilicate or "SK-40", from the Linde Division of Union Carbide and Carbon Corporation, was added to the resulting red solution. The SK-40 crystalline aluminosilicate support has pore diameters of about 13 Angstroms, a silica-to-alumina mole ratio of about 4.5:1 and a sodium oxide to alumina mole ratio of about 1:1. The reactor was purged with hydrogen for 20 minutes and then 30 ml of pentene-1 were fed to the system. The system was pressured from 35 psig to 125 psig with carbon monoxide and then to 303 psig with hydrogen at 130°F. Heating of the reactor was disconnected soon after the pentene-1 feed was introduced to the system. The pressure started to drop immediately after the system was pressured. The system was allowed to react for about 75 minutes. During this period the temperature of the reactor was kept at 130°–140°F. by the exothermicity of the reaction, and the pressure dropped gradually to 100 psig. At this stage, the system was repressured to 200 psig with carbon monoxide, and then to 300 psig with hydrogen for another 60 minutes. The pressure dropped again to 130 psig, and the reactor was quenched by running cold water through a cooling coil in the reactor. A dark-brown reaction mixture was discharged from the reactor, and the solid left inside of the reactor was rinsed with a fresh portion ( 30 ml) of benzene. The rinsed solid was saved for the second run. As shown in Table II, the pentene-1 feed was reacted in 83% conversion to give almost exclusively aldehydes, e.g., 26.2% of isohexanal and 68.8% n-hexanal. The conversion of the feed was calculated on the basis of the amount of unreacted pentene (and/or pentane) present in the discharged reaction mixture. The product was analyzed by means of gas chromatographic techniques.

The second run was started by injecting 22 ml of pentene-1 along with 20 ml benzene to the solid catalyst in the reactor. The reactor was pressured from 32 psig to 150 psig with carbon monoxide and then to 350 psig with hydrogen at 100°F. Heating of the reactor was controlled and the temperature and pressure of the system reached 146°F. and 370 psig within a 1½ hour period. After this induction period, the maximum pressure, 370 psig, dropped slowly to 245 psig by agitating the system at 146°F. for about 3 hours. A light-brown reaction mixture was removed from the reactor leaving a white solid inside of the reactor. Analysis of the product obtained from this second run was listed in Table III. The results from these two runs revealed that uncalcined SK-40 crystalline aluminosilicate promoted the hydroformylation of pentene-1 under much milder conditions that the system without SK-40 crystalline aluminosilicate.

EXAMPLE II

"SK-40", of the composition and pore diameter as set forth in Example I, which was calcined and had a surface area of about 870 square meters per gram, was used in this run. Tris(triphenylphosphine)rhodium(I) Chloride (0.4 m mole) was dissolved in 40 ml of benzene and 10 g. of the calcined SK-40 zeolite was introduced in the system. Immediately after the reactor was purged with hydrogen, 20 ml of pentene-1 was introduced to the reactor. The reactor was pressured to 190 psig with hydrogen, and then to 320 psig with carbon monoxide. The reactor was heated to attain 344 psig at 174°F. for a 2½ hour period. At this stage, the initial pressure drop was noticed. The reator was kept at 174°–198°F. for two hours, and the maximum pressure, 344 psig, dropped 150 psig in about 1½ hours. The system was again pressured from 150 psig to 150 psig with carbon monoxide and then to 350 psig with hydrogen. The reaction was allowed to proceed for ½ hour at 196°F. The pressure dorpped rather rapidly to 140 psig during this period. A brown reaction mixture was discharged from the reactor, and the product was analyzed by means of gas chromatographic technique. The pentene-1 feed was reacted in 82% conversion to yield almost exclusively hexanals (34.1% isohexanal, and 64.3% n-hexanal). The solid catalyst left inside of the reactor was used for two more runs. Details of the results obtained are listed in Tables I and II.

The second run was started by injecting 28 ml of pentene-1 to the solid catalyst, which was aged for 5½ hours. The reactor was pressured to 200 psig with hydrogen and then to 350 psig with carbon monoxide. The reaction was allowed to proceed in the absence of solvent. Heating was controlled to raise the temperature of the reactor to 198°F. in ~40 minutes. The original pressure was increased to 370 psig (the maximum pressure). The reactor was kept at 198°–260°F. for a 1½ hour period. The pressure dropped to 232 psig during this period. About 80% of the feed was reacted to give 29.2% isohexanal and 70.0% n-hexanal. The same reaction was repeated with the 23 hour aged catalyst in the third run as described in the second run. About 36% of the feed was converted to 29.1 area % isohexanal, 51.2% n-hexanal, 3.3% isohexanol, 13.1% n-hexanol and 3.2 % unidentified products. The change in the catalytic activity based on the conversion of feed may be attributed to leaching of the catalytic species from the SK-40 crystalline aluminosilicate base.

EXAMPLE III

Tris(triphenylphosphine)rhodium(I) chloride (0.6 m mole) was dissolved in 35 ml benzene and 3.1 g of the calcined Na-type Y crystalline aluminosilicate ("SK-40") of Example II was added to the solution. The system was purged with nitrogen and kept at room temperature for about one week. The red solution of $(\phi_3P)_3RhCl$ was slowly absorbed on the crystalline aluminosilicate phase to leave a lighter supernatant liquid. At the end of about a week period, the crystalline aluminosilicate assumed a brownish color and the supernatant liquid became almost completely colorless. This whole mixture was quantitatively transferred to a 300 cc autoclave reactor with the aid of a small portion of fresh benzene. After the system was purged witth hydrogen, 30 ml of pentene-1 was introduced and then the reactor was pressured with a premixed gas ($H_2$/CO, 1:1) to 400 psig and to 600 psig with hydrogen at 185°F. In 15 minutes the initial pressure drop was observed. The temperature and pressure of the reactor were 230°F. and 653 psig. The reactor was vigorously agitated at 230°–256°F. for a 45-minute period. The maximum pressure, 653 psig, dropped to 350 psig during this period. A brown reaction mixture was removed from the reactor along with some brown catalyst debris. About 51% of the pentene-1 feed was reacted to give exclusively hexanals.

The second run was started by introducing 30 ml of pentene-1 (without solvent) to the solid catalyst left inside of the autoclave from the preceding run. The reactor was pressured with a premixed gas ($H_2$/CO, 1:1) to 360 psig and then to 500 psig with hydrogen at 110°F. Heating of the reactor was controlled to raise the temperature of reactor to 200°F. in about an hour. The maximum pressure, 580 psig, dropped to 290 psig when the system was agitated at 200°–228°F. for an hour. A dark-brown reaction mixture with a small portion of catalyst debris was removed, and the product was analyzed by means of gas chromatographic technique. About 57% of the feed was reacted to 24.0% isohexanal, 54.5% n-hexanal, and 21.5% unidentified products.

The same reaction was repeated with the 21 hour aged catalyst in the third run as described in the second run. The catalytic activity based on the conversion of feed was maintained throughout these three runs over about a 22 hour period.

The results of these runs, listed in Tables I and II, indicate that the SK-40 crystalline aluminosilicate can be utilized as an effective supporting base for the rhodium oxo catalyst.

TABLE I

| Example No. | Run No. | Catalyst Composition | | | Catalyst Aged Hrs. | Reaction Conditions | | | |
|---|---|---|---|---|---|---|---|---|---|
| | | $(\phi_3P)_3RhCl$ mm | Support*[1] g | Solv. ml | | Pressure psig | Temperature °F. | Reaction Time Hrs. | $H_2$/CO |
| | | | | $C_6H_6$ | | | | | |
| I | 1st | 0.5 | 20 | 50 | — | 300–100 | 124–138 | ~2 | 1.9 |
| | 2nd | <0.5 | " | 20 | 2½ | 370–245 | 146 | 3 | 1.6 |
| II | 1st | 0.4 | 10**[2] | 40 | — | 350–140 | 174–198 | 2 | 1.5 |
| | 2nd | <0.4 | 10 | — | 5½ | 370–232 | 198–260 | 1½ | 1.3 |
| | 3rd | <0.4 | 10 | — | 23 | 515–438 | 206–252 | 7 | 1.4 |
| III | 1st | 0.6 | 3**[2] | 35 | — | 653–350 | 230–256 | ¾ | 2 |
| | 2nd | <0.6 | 3 | 0 | 18 | 580–290 | 200–228 | 1 | 1.2 |
| | 3rd | <0.6 | 3 | 0 | 21 | 450–365 | 280–242 | 1½ | 1.2 |

*[1]Uncalcined;
**[2]Calcined at 900°F.

TABLE II

| Example No. | Run No. | Feed g | Conv. % | iC$_6$—Al | nC$_6$—Al | iC$_6$—OH | nC$_6$—OH | Unknown | Heavy End |
|---|---|---|---|---|---|---|---|---|---|
| I | 1st | C$_5$=1 | 19.2 | 83 | 26.2 | 68.8 | — | — | 4.2 |
|   | 2nd | " | 14.0 | 79 | 24.6 | 69.2 | — | — | 6.3 |
|   | 1st | " | 19.2 | 82 | 34.1 | 64.3 | — | 0.2 | 1.4 |
| II | 2nd | " | 17.9 | 80 | 29.2 | 70.0 | — | — | 0.7 |
|   | 3rd | " | 18.0 | 36 | 29.1 | 51.2 | 3.3 | 13.1 | 3.2 |
|   | 1st | " | 18.9 | 51 | ~100 | — | — | — | — |
| III | 2nd | " | 18.9 | 57 | 24.0 | 54.5 | — | — | 21.5 |
|   | 3rd | " | 18.9 | 57 | 25.9 | 68.4 | — | — | 5.7 |

I claim:

1. In the process for the hydroformylation of olefin hydrocarbons of 2 to about 16 carbon atoms the improvement which comprises conducting said hydroformylation in contact with a catalyst composition consisting of a major amount of a solid, sodium form crystalline alumino-silicate support, said crystalline alumino-silicate support having a silicato alumina mole ratio of from about 2:1 to 12:1, a sodium oxide-to-alumina mole ratio of from about 0.7:1 to 1.1:1 and pore diameters of from about 6 to 15 Angstroms, and a minor amount of providing about 0.2 to about 0.6 weight percent rhodium, said rhodium composition having a mole ratio of ligand to metal of about 1.5:1 to 3:1, said ligand being R$_3$P in which each R is independently selected from the group consisting of phenylalkyl, alkylphenyl, phenyl, and alkyl groups having from 2 to about 16 carbon atoms.

2. The process of claim 1 wherein the hydroformylation is conducted at a temperature of from about 100° to 350°C. and a pressure of from about 500 to 2500 psig.

3. The process of claim 2 wherein said olefin is pentene.

4. The process of claim 1 wherein the catalyst contains about 0.2 to 0.6 weight percent of rhodium.

5. The process of claim 4 wherein the hydroformylation is conducted at a temperature of from about 100° to 350°C. and a pressure of from about 500 to 2500 psig.

6. The process of claim 5 wherein said olefin is pentene.

7. A process of claim 1 wherein said support has pore diameters of from 10 to 14 Angstroms, a silica-to-alumina mole ratio of from about 4:1 to 6:1 and a sodium oxide to alumina mole ratio of about 0.9:1 to 1:1 and said support is a Type Y zeolite, and the activity coefficient is greater than 100.

8. The process of claim 7 wherein the hydroformylation is conducted at a temperature from about 100° to 350°C. and a pressure of from about 500 to 2,500 psig.

9. The process of claim 8 wherein said olefin is pentene.

* * * * *

UNITED STATES PATENT OFFICE
CERTIFICATE OF CORRECTION

PATENT NO. : 3,940,447
DATED : February 24, 1976
INVENTOR(S) : Jin Sun Yoo

It is certified that error appears in the above-identified patent and that said Letters Patent are hereby corrected as shown below:

In Claim 1, column 9, line 20 change "silicato" to read --silica-to--.

Signed and Sealed this eighteenth Day of May 1976

[SEAL]

Attest:

RUTH C. MASON
*Attesting Officer*

C. MARSHALL DANN
*Commissioner of Patents and Trademarks*